(12) United States Patent
Baulcombe et al.

(10) Patent No.: US 8,759,102 B2
(45) Date of Patent: *Jun. 24, 2014

(54) SHORT RNA PRODUCING GENE SILENCING IN CELLS

(75) Inventors: David Charles Baulcombe, Norfolk (GB); Andrew John Hamilton, Helensburgh (GB)

(73) Assignee: Plant Bioscience Limited, Norfolk (GB)

( * ) Notice: Subject to any disclaimer, the term of this patent is extended or adjusted under 35 U.S.C. 154(b) by 1134 days.

This patent is subject to a terminal disclaimer.

(21) Appl. No.: 11/013,531

(22) Filed: Dec. 17, 2004

(65) Prior Publication Data

US 2005/0102710 A1    May 12, 2005

Related U.S. Application Data

(62) Division of application No. 10/805,804, filed on Mar. 22, 2004, now Pat. No. 8,097,710, which is a division of application No. 09/491,549, filed on Jan. 26, 2000, now Pat. No. 6,753,139.

(30) Foreign Application Priority Data

Oct. 27, 1999  (GB) .................................. 9925459.1

(51) Int. Cl.
| | | |
|---|---|---|
| C12N 5/07 | (2010.01) | |
| C12N 5/04 | (2006.01) | |
| C12N 1/00 | (2006.01) | |
| C12N 15/113 | (2010.01) | |
| C12N 15/63 | (2006.01) | |
| C12N 5/10 | (2006.01) | |

(52) U.S. Cl.
USPC ........ 435/419; 435/325; 435/320.1; 536/24.5

(58) Field of Classification Search
None
See application file for complete search history.

(56) References Cited

U.S. PATENT DOCUMENTS

| | | | |
|---|---|---|---|
| 5,624,803 A | 4/1997 | Noonberg et al. | |
| 5,801,154 A | 9/1998 | Baracchini et al. | |
| 5,998,203 A | 12/1999 | Matulic-Adamic et al. | |
| 6,107,094 A | 8/2000 | Crooke | |
| 6,365,731 B1 | 4/2002 | Brown et al. | |
| 6,506,559 B1 | 1/2003 | Fire et al. | |
| 6,573,099 B2 | 6/2003 | Graham | |
| 6,723,897 B2 | 4/2004 | Brown et al. | |
| 7,138,565 B2 * | 11/2006 | Waterhouse et al. | 800/285 |
| 2002/0086356 A1 | 7/2002 | Tuschl | |
| 2002/0160393 A1 | 10/2002 | Symonds | |
| 2002/0162126 A1 | 10/2002 | Beach | |
| 2003/0051263 A1 | 3/2003 | Fire | |
| 2003/0055020 A1 | 3/2003 | Fire | |
| 2003/0056235 A1 | 3/2003 | Fire | |
| 2003/0084471 A1 | 5/2003 | Beach | |
| 2003/0104401 A1 | 6/2003 | Lin | |
| 2003/0108923 A1 | 6/2003 | Tuschl | |
| 2003/0148519 A1 | 8/2003 | Engelke | |
| 2003/0157030 A1 | 8/2003 | Davis | |
| 2003/0190654 A1 | 10/2003 | Heidenreich | |
| 2003/0198627 A1 | 10/2003 | Arts | |
| 2003/0203868 A1 | 10/2003 | Bushman | |
| 2003/0204318 A1 | 10/2003 | Feldman | |
| 2004/0002077 A1 | 1/2004 | Taira | |
| 2004/0018999 A1 | 1/2004 | Beach | |
| 2004/0029275 A1 | 2/2004 | Brown | |
| 2004/0038921 A1 | 2/2004 | Kreutzer | |
| 2004/0053875 A1 | 3/2004 | Kreutzer | |
| 2004/0058886 A1 | 3/2004 | Scaringe | |
| 2004/0072779 A1 | 4/2004 | Kreutzer | |
| 2004/0086884 A1 | 5/2004 | Beach | |
| 2004/0086911 A1 | 5/2004 | Cabello | |
| 2004/0161777 A1 | 8/2004 | Baker | |
| 2004/0175703 A1 | 9/2004 | Kreutzer | |
| 2004/0180439 A1 | 9/2004 | Graham | |
| 2004/0192626 A1 | 9/2004 | McSwiggen | |
| 2004/0198640 A1 | 10/2004 | Leake | |
| 2004/0203145 A1 | 10/2004 | Zamore | |
| 2004/0224405 A1 | 11/2004 | Leake | |
| 2004/0229266 A1 | 11/2004 | Tuschl | |
| 2004/0235171 A1 | 11/2004 | Milner | |
| 2004/0248164 A1 | 12/2004 | Brown et al. | |
| 2004/0253604 A1 | 12/2004 | Lin et al. | |
| 2004/0259247 A1 | 12/2004 | Tuschl | |
| 2004/0259248 A1 | 12/2004 | Tuschl | |
| 2004/0266707 A1 | 12/2004 | Leake | |
| 2005/0020525 A1 | 1/2005 | McSwiggen | |
| 2005/0026278 A1 | 2/2005 | Tuschl | |
| 2005/0032733 A1 | 2/2005 | McSwiggen | |
| 2005/0166289 A1 | 7/2005 | Chiang et al. | |
| 2005/0260754 A1 | 11/2005 | Kock et al. | |

FOREIGN PATENT DOCUMENTS

| | | |
|---|---|---|
| EP | 1 080 208 B1 | 3/2001 |
| EP | 1 144 623 | 10/2001 |
| WO | WO-94/01550 | 1/1994 |
| WO | WO-99/29840 | 6/1999 |
| WO | WO 01/75164 A2 | 10/2001 |

OTHER PUBLICATIONS

Horsch et al., Science, 1985, vol. 227, pp. 1229-1231.*
Goldbach et al., Meth. Plant Biochem., 1997, vol. 10b, pp. 103-120.*
Bourque et al., Plant Molecular Biology, 1992, vol. 19, pp. 641-647.*
Heard et al., Nucl. Acids Res., 1995, vol. 23, pp. 1970-1976.*
Fire, Andrew Z., Nobel Lecture, Dec. 8, 2006.*
Tuschl. et al., Genes Dev., 13: 3191-3197 (1999).*
Ngo et al., PNAS (1998), 95: 14687-14692.*
Zamore et al., Cell 101: 25-33 (2000).*
Hamilton and Baulcombe, Science (1999) 286: 950-952.*

(Continued)

*Primary Examiner* — David T Fox
*Assistant Examiner* — Steven Bernacki
(74) *Attorney, Agent, or Firm* — Morrison & Foerster LLP

(57) ABSTRACT

Cells that have been exogenously supplied with short RNA molecules to effect posttranscriptional gene silencing are described.

16 Claims, No Drawings

(56) References Cited

OTHER PUBLICATIONS

Fire et al., Nature (1998) 391: 806-811.*
Wianny et al., Nature Cell Biology (2000) 2: 70-75.*
English, J.J. et al., "Suppression of Virus Accumulation in Transgenic Plants Exhibiting Silencing of Nuclear Genes"; The Plant Cell, 8: 179-188 (1996).
Prins, M. et al., "RNA-mediated virus resistance in transgenic plants"; Arch Virol 141: 2259-2276 (1996).
Sijen,T. et al., "RNA-Mediated Virus Resistance: Role of Repeated Transgenes and Delineation of Targeted Regions"; The Plant Cell, 8: 2277-2294 (1996).
Smith, H.A. et al., "Transgenic Plant Virus Resistance Mediated by Untranslatable Sense RNAs: Expression, Regulation, and Fate of Nonessential RNAs"; The Plant Cell, 6: 1441-1453 (1994).
Elmayan, T. et al., "Expression of single copies of a strongly expressed 35S transgene can be silenced post-transcriptionally"; The Plant Journal, 9(6): 787-797 (1996).
Baulcombe, D.C. et al., "Ectopic pairing of homologous DNA and post-transcriptional gene silencing in transgenic plants"; p. 173-180, Curr. Op. Biotech., Jul. 1996.
Kunz, C. et al., "Developmentally regulated silencing and reactivation of tobacco chitinase transgene expression"; The Plant Journal, 10(3): 437-450 (1996).
Van Blokland, R. et al., "Transgene-mediated suppression of chalcone synthase expression in *Petunia hybrida* results from an increase in RNA turnover"; The Plant Journal, 6(6): 861-877 (1994).
Schiebel, W. et al., "RNA-directed RNA Polymerase from Tomato Leaves—I Purification and Physical Properties", The Journal of Biological Chemistry, 263(16): 11851-11857 (1993).
Schiebel, W. et al., "RNA-directed RNA Polymerase from Tomato Leaves—II Catalytic in Vitro Properties", The Journal of Biological Chemistry, 268(16): 11858-11867 (1993).
Baulcombe, D.C., "Mechanisms of Pathogen-Derived Resistance to Viruses in Transgenic Plants"; The Plant Cell, 8: 1833-1844 (1996).
Lindbo, J.A. et al., "Pathogen-Derived Resistance to a Potyvirus: Immune and Resistant Phenotypes in Transgenic Tobacco Expressing Altered Forms of a Potyvirus Coat Protein Nucleotide Sequence"; Molecular Plant-Microbe Interactions, 5(2): 144-153 (1992).
Lindbo, J.A. et al., "Untranslatable Transcripts of the Tobacco Etch Virus Coat Protein Gene Can Interfere with Tobacco Etch Virus Replication in Transgenic Plants and Protoplasts"; Virology, 189: 725-733 (1992).
Stam, M. et al., "The Silence of Gene in Transgenic Plants"; Annals of Botany, 79: 3-12 (1997).
Elbashir, S.M. et al., "Duplexes of 21-nucleotide RNAs mediate RNA interference in cultured mammalian cells"; Nature, 411: 494-498 (2001).
Waterhouse, P.M. et al., "Role of short RNAs in gene silencing"; Trends in Plant Science, 6(7): 297-301 (2001).
Lindbo, J.A. et al., "Induction of Highly Specific Antiviral State in Transgenic Plants: Implications for Regulation of Gene Expression and Virus Resistance"; The Plant Cell, vol. 5, 1749-1759, Dec. 1993.
Flavell, R.B. et al., "Inactivation of gene expression in plants as a consequence of specific sequence duplication"; Proc. Natl. Acad. Sci. USA, vol. 91, 3490-3496, Apr. 1994.
Grierson, D. et al., "Does co-suppression of sense genes in transgenic plants involve antisense RNA"; TIBTECH, vol. 9, 122-123, Apr. 1991.
Metzlaff, M. et al., "RNA-Mediated RNA Degradation and Chalcone Synthase A Silencing in *Petunia*", Cell, vol. 88, 845-854, Mar. 21, 1997.

Dougherty, W.G. et al., "Transgenes and gene suppression: telling us something new?"; Current Opinion in Cell Biology 7, 399-405, 1995.
Overheads from talk given by one of the inventors on Feb. 27, 1999 at EMBO workshop on "Post-transcriptional regulation of gene expression in plants"; Feb. 25-28, 1999 conducted at Leysin, in Switzerland.
Poster given at meeting: Molecular Plant Microbe Interactions (MPMI), 9th International Congress, Jul. 25-30, 1999.
Waterhouse, P. et al. "Virus resistance and gene silencing in plants can be induced by simultaneous expression of sense and antisense RNA"; Proc. Natl. Acad. Sci. USA, 95: 13959-13964 (1998).
Wassenegger, M. et al. "Model for RNA-mediated gene silencing in higher plants"; Plant Molecular Biology, 37: 349-362 (1998).
Hamilton, A.J. et al. "Species of Small Antisense RNA in Post-transcriptional Gene Silencing in Plants"; Science, 286: 950-952 (1999).
Lee, et al. "The *C. elegans* Heterochronic Gene lin-4 Encodes Small RNA's with Antisense Complementarity to lin-14"; Cell, 75: 843-854 (1993).
Manche et al., Molecular and Cellular Biology (1992) 12(11):5238-5248.
Tracewell et al., Toxicology and Applied Pharmacology (1995) 135:179-184.
Boutla et al., Nucl. Acids Res. (2002) 30:1688-1694.
Stratagene pBluescript II Phagemid Vectors Instruction Manual for Catalog # 212207, downloaded from the Stratagene, Inc. website on Jan. 11, 2007.
BLAST analysis from NCBI of nucleic acid sequence "cccggtac-ccagcttttgttccc" completed on Jan. 11, 2007.
Bridge et al., Nature Genetics (2002) 34(3):263-264.
Elbashir et al., The EMBO Journal (2001) 20(23):6877-6888.
Liu et al., Analytical Biochemistry (1999) 270:112-122.
Zhang et al., Cell (2004) 118:57-68.
Opalinska et al., Nature Reviews Drug Discovery (2002) 1:503-514.
Bevilacqua et al., Biochemistry (1996) 35:9983-9994.
Klahre et al., PNAS USA (2002) 99:11981-11986.
Hamilton et al., Plant J. (1998) 15:737-746.
Claycomb and Lanson, Biochem. J. (1987) 247:701-706.
Lee et al., Cell (1993) 75:843-854.
Schena et al., Trends in Biotechnology (1998) 16:301-306.
Hamilton et al., EMBO J. (2002) 21:4671-4679.
Overhoff et al., Nucleic Acids Research (2004) 32:e170.
Babiarz et al., Genes & Development (2008) 22:2773-2785.
Watanabe et al., Nature (2008) 453:539-544.
Sontheimer and Carthey, Cell (2005) 122:9-12.
Cullen, Nature Genetics (2005) 37(11):1163-1165.
Krichevsky and Kosik, PNAS (2002) 99(18):11926-11929.
Non-Final Office Action for U.S. Appl. No. 11/013,315, mailed on Feb. 9, 2009, 27 pages.
Klahre et al., PNAS (2002) 99:11981-11986.
Elbashir et al., Genes Dev. (2001) 15:188-200.
Fire, TIG (1999) 15:358-363.
Fire et al., Nature (1998) 391:806-811.
Minks et al., J. Biol. Chem. (1978) 254:10180-10183.
Palauqui et al., Curl. Biol. (1999) 9:59-65.
Parrish et al., Mol. Cell (2006) 6:1077-1087.
Torrence, Pharmac. Ther. A (1977) 2:1-88.
Voinnet et al., Cell. (1998) 95:177.
Wang et al., Microbiol. Mol. Biol. Rev. (2004) 68:432-452.
Wianny et al., Cell Biol. (2000) 2:70-75.

* cited by examiner

SHORT RNA PRODUCING GENE SILENCING IN CELLS

TECHNICAL FIELD

The present invention relates generally to methods and materials for use in achieving and detecting gene silencing, particularly post-transcriptional gene silencing, in an organism.

PRIOR ART

Methods of detecting and efficiently achieving gene silencing are of great interest to those skilled in the art.

Post-transcriptional gene silencing (PTGS) is a nucleotide sequence-specific defense mechanism that can target both cellular and viral mRNAs. PTGS occurs in plants and fungi transformed with foreign or endogenous DNA and results in the reduced accumulation of RNA molecules with sequence similarity to the introduced nucleic acid (1, 2).

PTGS in plants can be suppressed by several virus-encoded proteins (6) and is closely related to RNA-mediated virus resistance and cross-protection in plants (7, 8). Therefore, PTGS may represent a natural antiviral defense mechanism and transgenes might be targeted because they, or their RNA, are perceived as viruses. PTGS could also represents a defense system against transposable elements and may function in plant development (9-11). To account for the sequence specificity, and post-transcriptional nature of PTGS it has been proposed that antisense RNA forms a duplex with the target RNA thereby promoting its degradation or interfering with its translation (12).

One problem which exists in actually utilising efficient gene silencing, for instance via anti-sense mechanisms, is selecting appropriate regions to target. This problem has been reviewed in the literature (see Szoka (1997) Nature Biotechnology 15: 509; Eckstein (1998) Nature Biotechnology 16: 24). Proposed solutions to selecting good target regions include computational analysis (Patzel and Sczakiel (1998) Nature Biotechnology 16: 64-68) or Rnase H cleavage using chimeric anti-sense oligonucleotides (see Ho (1996) Nucleic Acid Res 24: 1901-1907; Ho et al (1998) Nature Biotechnology 16: 59-62). Other groups have used wide array of oligonucleotides to select those which form heteroduplexes (see Milner et al (1997) Nature Biotechnology 15: 537-541).

DISCLOSURE OF THE INVENTION

The present inventors have investigated PTGS of target genes initiated by a variety of silencing mechanisms in different organisms, and have established that in every case a previously uncharacterised species of antisense RNA complementary to the targeted mRNA was detected. These RNA molecules were of a uniform length, estimated at around 25 nucleotides, and their accumulation required either transgene sense transcription or RNA virus replication. Corresponding sense RNA molecules were also detected.

There have been no previous reports of such short sense and antisense RNA molecules (hereinafter, collectively, SRMs) that are detected exclusively in organisms exhibiting PTGS, possibly because (owing to their size) they could not have been readily detected by routine RNA analyses.

It appears that the SRMs may be synthesized from an RNA template and represent a specificity determinant and molecular marker of PTGS. Because of their correlation with PTGS and the nature of the molecules (short complementary molecules which could base pair with the target RNAs) they are believed to represent a signal and/or inducer or activator of PTGS.

The identification of this species by the present inventors may be utilised by those skilled in the art in a variety of methods and processes which are discussed in more detail below. Generally speaking the present invention provides, inter alia, methods of identifying and screening for gene silencing and particular silenced genes in organisms; processes for producing or isolating silencing agents, and such isolated agents themselves; methods for selecting target regions of nucleic acids which it is desired to silence and methods for silencing target genes using the agents or target regions generated as above. Also included are relevant materials (e.g. nucleic acids, constructs, host cells, transgenic plants, silenced organisms) and methods of use of these.

Importantly, the disclosure herein provides evidence that SRMs may be a common mediator of PTGS in both plants and higher organisms, such as the nematode discussed in the Examples hereinafter. It was previously known that double stranded RNA induces a similar effect to plant PTGS in nematodes, insects (4) and protozoa (5). For instance PTGS has been demonstrated in *Caenorhabditis elegans* (a nematode worm) using DsRNA introduced into the worms by microinjection, imbibing or by allowing the worms to eat bacteria (*E. coli*) which are synthesizing dsRNA. There was also some evidence that in some examples of PTGS in plants and dsRNA interference in nematodes, a signal is produced which spreads and amplifies the silencing beyond the point of introduction of the original inducer of silencing. Although there were known to be certain similarities between the DsRNA induced silencing in nematodes and the causes of PTGS in plants, there was no clear evidence that the two are related.

Aspects of the invention will now be discussed in more detail.

Thus in one aspect of the present invention there is provided a method of detecting, diagnosing, or screening for gene silencing in an organism, which method comprises the steps of:

(i) obtaining sample material from the organism,
(ii) extracting nucleic acid material therefrom,
(iii) analysing the extracted nucleic acid in order to detect the presence or absence of SRMs therein, The result of the analysis in step (iii) may be correlated with the presence of silencing in the organism.

The 'sample' may be all or part of the organism, but will include at least some cellular material.

The term 'SRMs' is used to describe the short RNA molecules described herein which are approximately 25 nucleotides in length. The size appears to be very characteristic, being estimated as approximately 25 nucleotides in all the cases tested (relative to the same molecular size markers when assessed by chromatography). However, it may be slightly more or less than this characteristic length (say plus or minus 1, 2, 3, 4 or 5 nucleotides) and where the term '25 nt RNA' is used herein, it will be understood by those skilled in the art that the comments would apply equally in the event that the SRMs do not have this precise length.

Indeed the precise length may not be important, since the disclosure herein permits the identification, isolation and utilisation of SRMS in any case.

In performing the invention, it may be preferred to analyse or otherwise utilise short anti-sense RNA molecules (SARMs) rather than short sense RNA molecules (SSRMs). Nonetheless, where reference is made herein to SARMs (except where context clearly suggests otherwise) it will be appreciated by those skilled in the art that the SSRMs may also be used.

In particular, the SRMs methodology may be used as an indicator of PTGS. As is well known to those skilled in the art, PTGS occurs post-transcriptionally: i.e. the transcription rates of the suppressed genes are unaffected. The term 'gene' is used broadly to describe any sequence which is suitable for translation to a protein.

Thus the presence of SRMs can be used as a diagnostic test for the existence of PTGS.

In one embodiment of this aspect there is disclosed a method of detecting or identifying the silencing of a target gene in an organism, which method further comprises characterising any SRMs which are present. It should be noted that PTGS effects are very dominant. In principle the presence of SRMs may indicate the silencing of more than one gene, providing that they have sufficient homology.

'Characterised' and 'characterising' does not necessarily imply complete sequencing, although this may be preferred. In order to detect silencing of a known sequence, the SRMs may be fully or partially sequenced, or sequence identity or similarity may be inferred from e.g. blotting.

Applications for such a diagnostic test will depend on the organism in question. For instance, in plants, since PTGS is the basis for a lot of pathogen derived resistance (PDR), GM field crops (e.g. individuals, or populations) engineered for PDR could be monitored "in field" by checking for the existence of 25 nt RNA to make sure that the PDR was still operating prior to the attack by the virus.

Similarly, crops depending upon co-suppression for the knockout of a particular plant gene to achieve a specific modified trait could be assayed for the continued function of PTGS by checking the presence of 25 nt RNA against the intended target. Such an assay may be particularly useful in view of evidence that transgenes have a tendency to become transcriptionally inactivated over the generations. PTGS depends upon transcription of the initiating transgene to function and so if this gets reduced the PTGS will begin to fail. Monitoring 25 nt RNA provides a quick way to test the lines. Non-limiting Examples of silenced genes which could be monitored in this way include any of those which have already been shown to be suppressible by PTGS in the literature. These may include, for example, chalcone synthase or petunia or polygalacturonase of tomato (Jorgensen, R. A. (1995), *Science,* 268: 686-691, Hamilton, A. J., et al (1995), *Current Topics In Microbiology and Immunology,* 197: 77-89).

It is also possible that the process of PTGS underlies certain plant developmental processes. If there are plant genes which are being targeted naturally as a result of PTGS in order to satisfy some plant developmental programme, a 25 nt RNA corresponding to sequences from these genes may be detectable.

Thus, in this embodiment, the SRMs may be used to identify and isolate an unknown target. This could be achieved by analysing the 25 nucleotide fraction of RNA from a plant, tagging it with a marker (e.g. a radioactive one) and then using this radioactive RNA to probe a library of plant genes. This probe will anneal to genes which are undergoing PTGS in the plant, which genes can then be further analysed or characterised if required. Such genes, inasmuch as they are novel, represent a further aspect of the present invention.

In a further aspect of the present invention, there is disclosed a process for producing or isolating short RNA molecules. As discussed above, SRMs may not be readily detected by routine RNA analyses, particularly those which include a step in which such molecules are 'lost' (for instance SRMS may not be efficiently retained on silica columns which are used to isolate longer molecules such as mRNAs). A preferred process is set out in the Examples hereinafter. Broadly speaking, the processes provided divide into two parts: extraction/purification and detection.

For extraction, initial steps may be performed using conventional RNA extraction methods and kits appropriate to the organism in question, modified as required to ensure that SRMs are retained at each step.

In order to enhance purification of short RNAs, the extraction may optionally be followed by one or more of the following steps:
(i) filtration (e.g. through Centricon 100 concentrators (Amicon) or similar),
(ii) differential precipitation (e.g. with 5% polyethylene glycol (8000)/0.5M NaCl)
(iii) ion exchange chromatography (e.g. using Qiagen columns).

These steps enrich and purify the short RNAs to greater degrees than is obtained with the routine rRNA extraction method alone, and may be performed in conventional manner using, if required, proprietary reagents.

It should be noted that there is no requirement that the short RNAs be purified to homogeneity, provided only that they are capable of detection.

Regarding detection, because of their small size the method for this is not the usual one for "RNA gel blot analysis" although the principle is the same i.e. separation of the RNA molecules according to size by electrophoresis through a gel.

Preferably the gel is a 15% polyacrylamide gel containing 7M urea as a denaturant and TBE (0.5×) as a buffer.

The RNAs are preferably transferred to a hybridisation membrane by electrophoresis (rather than the more conventional capillary blot). Once the RNA is on the membrane, it is covalently attached to it by UV irradiation. The membrane is then placed in "prehybridisation solution" for a short time.

Radioactive probe may be prepared using standard techniques. However, preferably, it is made as a single stranded RNA molecule transcribed in vitro from an appropriate plasmid DNA templates. The length of the probe may, preferably, be shortened by limited hydrolysis before adding to the prehybridisation solution; this may reduce non-sequence specific binding of probe to the membrane.

The hybridisation of the probe to its target is allowed to proceed at a stringency level (specific temperature, salt concentration and the concentration of formamide in the prehybridisation solution) appropriate to the requirements of the process. For instance low temperature, high salt, no formamide equals a low stringency, which may permit short probes or probes with imperfect homology to the target to hybridise with the target. Conversely high temperature, low salt and formamide mean high stringency with only lengthy duplexes stable under these conditions. Preferred conditions are 45% formamide, 7% SDS, 0.3M NaCl, 0.05M $Na_2HPO_4$/$NaH_2PO_4$ (pH7), 1×Denhardt's solution, and single stranded heterologous nucleic acid (e.g. derived from salmon sperm).

This is one preferred process of purifying (or partially purifying) SRMs for the purpose of detection and/or further characterising e.g. for sequencing. However it should be understood that the present invention is in no way limited to this particular format, and others methods for SRMs analysis, such as those which may be devised in the future, will also be encompassed.

The process described above may form part of a more extensive process for producing or isolating a silencing agent for a target gene, which silencing agent is a preferably a SRM, the process comprising the steps of:

(i) silencing a target gene in an organism,
(ii) performing a process as described above in order to isolate a SRM appropriate for that gene.

'Silencing agent' in this context may be one or more of an inducer, signal, or specificity determinant of gene silencing, particularly PTGS. Preferably this will be a SARM (as opposed to a SSRM). Isolated silencing agents obtained or obtainable by this method, inasmuch as they are novel, form a further aspect of the present invention.

The initial silencing step may be achieved by any conventional method appropriate to the organism in question. For instance in plants it could be by silencing of endogenous, homologous genes (co-suppression—see, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020). Further refinements of the gene silencing or co-suppression technology may be found in WO95/34668 (Biosource); Angell & Baulcombe (1997) The EMBO Journal 16, 12:3675-3684; and Voinnet & Baulcombe (1997) Nature 389: pg 553 (systemically induced transgene silencing). Other options include transgene silencing; RNA mediated defense against viral infection, and transgenic, homology-dependent, virus resistance, or use of dsRNA in the case of nematodes.

In a further aspect of the present invention there is disclosed a method for identifying or selecting a target region of a gene, which gene it is desired to silence, which method comprises:

(i) silencing the target gene in an organism,
(ii) performing a process as described above in order to isolate a SRM appropriate for that gene,
(iii) identifying a region in the sequence of the gene which corresponds to the sequence of the SRM.

The region may identified most readily by comparing the sequence of the SRM with the sequence of the gene; however any appropriate method may be used (e.g. RNAase protection). If several SRMs are isolated, then several target regions may be identified.

As described in the introduction, this method provides an alternative to e.g. computational analysis in order to identify the most suitable site on e.g. an mRNA corresponding to a target gene, for targeting for silencing e.g. with an anti-sense construct. With the information obtained using the methods and processes herein about, more efficient antisense reagents (not necessarily RNAs) may be produced which are tailored such that they would be recognised and used by the PTGS machinery of the organism.

In a further aspect of the present invention there is disclosed a method of silencing a target gene in an organism which utilises the methodology described above.

"Silencing" in this context is a term generally used to refer to suppression of expression of a gene. The degree of reduction may be so as to totally abolish production of the encoded gene product, but more usually the abolition of expression is partial, with some degree of expression remaining. The term should not therefore be taken to require complete "silencing" of expression. It is used herein where convenient because those skilled in the art well understand this.

In one embodiment, the method comprises introducing anti-sense molecules [SARMs] appropriate for the target gene into the organism in order to induce silencing. This could be done, for instance, by use of transcribable constructs encoding the SARMs.

In a related embodiment, the silencing may be achieved using constructs targeting those regions identified by the SRMs-based method disclosed above. Such constructs may e.g. encode anti-sense oligonucleotides which target all are part of the identified region, or a region within 1, 2, 3, 4, 5, 10, 15 or 20 nucleotides of the identified region.

Suitable target genes for silencing will occur to those skilled in the art as appropriate to the problem in hand. For instance, in plants, it may be desirable to silence genes conferring unwanted traits in the plant by transformation with transgene constructs containing elements of these genes. Examples of this type of application include silencing of ripening specific genes in tomato to improve processing and handling characteristics of the harvested fruit; silencing of genes involved in pollen formation so that breeders can reproducibly generate male sterile plants for the production of F1 hybrids; silencing of genes involved in lignin biosynthesis to facilitate paper making from vegetative tissue of the plant; silencing of genes involved in flower pigment production to produce novel flower colours; silencing of genes involved in regulatory pathways controlling development or environmental responses to produce plants with novel growth habit or (for example) disease resistance; elimination of toxic secondary metabolites by silencing of genes required for toxin production. In addition, silencing can be useful as a means of developing virus resistant plants when the transgene is similar to a viral genome.

As described above, the disclosure herein provides evidence that SRMs may be a common mediator of PTGS in both plants and higher organisms. These new findings can be utilised, inter alia, in that it now appears that induction of SRMs (particularly SARMs) with an appropriate specificity in one organism (say, a plant) may be used to silence an appropriate target gene in another organism (say, a predator) which comes into contact with that plant.

In one aspect of the invention there is provided a method for targeting a gene in a first organism, which method comprises generating a SARMs silencing agent in a second organism, and introducing the SARMs into the first organism.

The SARMs may be generated by any appropriate silencing method. Preferably the target gene will be one which is not an endogenous gene in the second organism (but preferably is endogenous to the first). The 'contact' may be ingestion, injection, or any other method of administration. How, precisely, the method is performed will depend on the organisms and genes involved.

For instance, in the case of plants and plant predators, it is known that the systemic signal of PTGS travels out of plant cells into the phloem (sap) of plants and induces silencing in previously non-silencing parts of the plant. In the light of the present disclosure it is clear that, since plant parasitic nematodes feed directly upon the sap and contents of plant cells, they will ingest the signal and inducer of PTGS (i.e. SARMs) in the plant.

As shown in the Examples below, it appears that the same type of SARMs are present in *C. elegans* which are undergoing PTGS induced by the ingestion of dsRNA. This implies that the mechanism of PTGS in plants and nematode is similar if not identical. Thus plant SARMs may trigger the PTGS of any similar sequences present in the worm. Therefore when the nematode feeds on the plant, and eats the PTGS signal, if there is homology between the plant's transgene from which the PTGS signal derived and a nematode gene, PTGS of that gene ought to be triggered in the worm.

Where the targeted gene is an essential gene, this method provides a means of controlling or killing plant predators or pests. Naturally, more than one gene can be targeted at once.

It may be desirable that the targeted gene is one which is either not present, or not important, in the wild-type plant or other potential consumers of the plant i.e. is nematode specific gene, such as a nematode protease gene. This gives the method a high degree of specificity.

Interestingly *C. elegans* is a nematode distantly related to the nematodes that parasitise plants. Since dsRNA induced PTGS is conserved between nematodes, protozoa and insects it is likely that these other organisms which support PTGS may be susceptible to SARMs.

DsRNA interference has also been shown to work in insects and transgene induced PTGS works in fungi, so it is likely that this is a mechanism that is broadly conserved across the kingdoms. This implies that any organism that directly feeds off plant cellular contents or extracellular components such as sap could ingest PTGS specific SARMs. If these have sequence homology with genes resident in the parasite, PTGS of these genes could be initiated.

Thus insect specific genes (e.g. from aphids) represent a further target. Most preferable would be those insect genes or sequences not found in beneficial insects, such a ladybirds.

Other targets include genes specific for plant parasites of plants which feed off the host plant.

Specifically regarding higher animals (e.g. mammals, fish, birds, reptiles etc.) methods of the present invention include, inter alia:
(i) methods for detecting or diagnosing gene silencing, or silencing of particular genes, in the animal by using SRMs as described above,
(ii) methods for identifying silenced genes in the animal by using SRMs as described above,
(iii) methods for selecting target sites on genes to be silenced using SRMs as described above,
(iv) method for silencing a target gene in the animal, either directly, or through an animal-derived transgene in a second organism (e.g. a plant) as described above.

Generally speaking target genes in animals may be those whose functional impairment beings therapeutic benefits. Typical genes of interest may be (for instance) those involved apoptosis, cancer, cell-cycle regulation, neurological processes, signal transduction etc. Examples and references can be found in the Oncogene Research Products 1999 General Catalog, pp 21-265, available from Oncogene Research Products, 84 Rogers Street, Cambridge, Mass. 02142, U.S. Preferred examples include oncogenes, transcriptional regulators, pocket proteins, members of the MHC superfamily (to produce allotypic organs) etc.

Some further aspects and applications for the present invention will now be discussed.

According to one aspect of the present invention there is provided, preferably within a vector suitable for stable transformation of a plant cell, a DNA construct in which a promoter is operably linked to DNA for transcription in a plant cell to generate either:
(i) a SARM as described above, or
(ii) an anti-sense RNA molecule selected to target a region identified by the SRM-based methods discussed above.

Generally speaking, such constructs may be used to silence genes within plants, or within organisms predating or being administered material from plants, in the terms discussed above.

Anti-sense partial gene sequences selected in accordance with SRM-based methods may be used analogously to those previously used in the art. See, for example, Rothstein et al, 1987; Smith et al, (1988) *Nature* 334, 724-726; Zhang et al, (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell, (1994) *PNAS USA* 91, 3490-3496. Generally the selected sequence will be less than 50, 40, 30, 25, or 20 nucleotides. It may be preferable that there is complete sequence identity in the targeting (e.g. foreign) sequence in the construct and the target sequence in the plant, although total complementarity or similarity of sequence is not essential.

Again, generally speaking, plants and associated methods and processes which form a part of the present invention are either those which:
(i) are transformed with the 'targeting' anti-sense vectors such as those described above, for instance so as to silence an (endogenous) target gene in the plant or perhaps a viral gene, or
(ii) are transformed with transgenes taken from other organisms such as to induce transgene silencing and thereby generate SARMs which can be used to silence a target gene in that other organism, or
(iii) are transformed with vectors which encode SARMs directly, which can be used for either purpose.

The general methodology discussed below will be applicable to all of these applications.

A vector which contains the construct may be used in transformation of one or more plant cells to introduce the construct stably into the genome, so that it is stably inherited from one generation to the next. This is preferably followed by regeneration of a plant from such cells to produce a transgenic plant. Thus, in further aspects, the present invention also provides the use of the construct or vector in production of a transgenic plant, methods of transformation of cells and plants, plant and microbial (particularly *Agrobacterium*) cells, and various plant products.

The function of the promoter in the construct is to ensure that the DNA is transcribed into RNA containing the viral sequences. By "promoter" is meant a sequence of nucleotides from which transcription may be initiated of DNA operably linked downstream (i.e. in the 3' direction on the sense strand of double-stranded DNA). A promoter "drives" transcription of an operably linked sequence.

"Operably linked" means joined as part of the same nucleic acid molecule, suitably positioned and oriented for transcription to be initiated from the promoter.

Preferred promoters may include the 35S promoter of cauliflower mosaic virus or the nopaline synthase promoter of *Agrobacterium tumefaciens* (Sanders, P. R., et al (1987), *Nucleic Acids Res.*, 15: 1543-1558). These promoters are expressed in many, if not all, cell types of many plants. Depending on the target gene of amplicon gs, other promoters including those that are developmentally regulated or inducible may be used. For example, if it is necessary to silence the target gene specifically in a particular cell type the construct may be assembled with a promoter that drives transcription only in that cell type. Similarly, if the target gene is to be silenced following a defined external stimulus the construct may incorporate a promoter that is be activated specifically by that stimulus. Promoters that are both tissue specific and inducible by specific stimuli may be used. Suitable promoters may include the maize glutathione-S-transferase isoform II (GST-II-27) gene promoter which is activated in response to application of exogenous safener (WO93/01294, ICI Ltd).

An additional optional feature of a construct used in accordance with the present invention is a transcriptional terminator. The transcriptional terminator from nopaline synthase gene of *agrobacterium tumefaciens* (Depicker, A., et al (1982), *J. Mol. Appl. Genet.*, 1: 561-573) may be used. Other suitable transcriptional terminators will be well known to those skilled in the art.

Those skilled in the art are well able to construct vectors (including those based on 'naked' DNA) and design protocols for recombinant gene expression. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Protocols in Molecular Biology*, Second Edition, Ausubel et al. eds., John Wiley & Sons, 1992.

Specific procedures and vectors previously used with wide success upon plants are described by Bevan, Nucl. Acids Res. (1984) 12, 8711-8721), and Guerineau and Mullineaux, (1993) Plant transformation and expression vectors. In: Plant Molecular Biology Labfax (Croy RRD ed) Oxford, BIOS Scientific Publishers, pp 121-148.

For introduction into a plant cell, the nucleic acid construct may be in the form of a recombinant vector, for example an *Agrobacterium* binary vector. Microbial, particularly bacterial and especially *Agrobacterium*, host cells containing a construct according to the invention or a vector which includes such a construct, particularly a binary vector suitable for stable transformation of a plant cell, are also provided by the present invention.

Nucleic acid molecules, constructs and vectors according to the present invention may be provided isolated and/or purified (i.e. from their natural environment), in substantially pure or homogeneous form, or free or substantially free of other nucleic acid. Nucleic acid according to the present invention may be wholly or partially synthetic. The term "isolate" encompasses all these possibilities.

An aspect of the present invention is the use of a construct or vector according to the invention in the production of a transgenic plant.

A further aspect provides a method including introducing the construct or vector into a plant cell such that the construct is stably incorporated into the genome of the cell.

Any appropriate method of plant transformation may be used to generate plant cells containing a construct within the genome in accordance with the present invention. Following transformation, plants may be regenerated from transformed plant cells and tissue.

Successfully transformed cells and/or plants, i.e. with the construct incorporated into their genome, may be selected following introduction of the nucleic acid into plant cells, optionally followed by regeneration into a plant, e.g. using one or more marker genes such as antibiotic resistance. Selectable genetic markers may be used consisting of chimeric genes that confer selectable phenotypes such as resistance to antibiotics such as kanamycin, hygromycin, phosphinotricin, chlorsulfuron, methotrexate, gentamycin, spectinomycin, imidazolinones and glyphosate.

When introducing a nucleic acid into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material should occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser—see attached) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d). Physical methods for the transformation of plant cells are reviewed in Oard, 1991, *Biotech. Adv.* 9: 1-11.

*Agrobacterium* transformation is widely used by those skilled in the art to transform dicotyledonous species. Recently, there has been substantial progress towards the routine production of stable, fertile transgenic plants in almost all economically relevant monocot plants (Toriyama, et al. (1988) *Bio/Technology* 6, 1072-1074; Zhang, et al. (1988) *Plant Cell Rep.* 7, 379-384; Zhang, et al. (1988) *Theor Appl Genet* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828). In particular, *Agrobacterium* mediated transformation is now emerging also as an highly efficient transformation method in monocots (Hiei et al. (1994) *The Plant Journal* 6, 271-282).

The generation of fertile transgenic plants has been achieved in the cereals rice, maize, wheat, oat, and barley (reviewed in Shimamoto, K. (1994) *Current Opinion in Biotechnology* 5, 158-162; Vasil, et al. (1992) *Bio/Technology* 10, 667-674; Vain et al., 1995, *Biotechnology Advances* 13 (4): 653-671; Vasil, 1996, *Nature Biotechnology* 14 page 702).

Microprojectile bombardment, electroporation and direct DNA uptake are preferred where *Agrobacterium* is inefficient or ineffective. Alternatively, a combination of different techniques may be employed to enhance the efficiency of the transformation process, e.g. bombardment with *Agrobacterium* coated microparticles (EP-A-486234) or microprojectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cel Genetics of Plants*, Vol I, II and III, *Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practicing the invention with a particular methodology of choice. It will be apparent to the skilled person that the particular choice of a transformation system to introduce nucleic acid into plant cells is not essential to or a limitation of the invention, nor is the choice of technique for plant regeneration.

Also according to the invention there is provided a plant cell having incorporated into its genome a DNA construct as disclosed. A further aspect of the present invention provides a method of making such a plant cell involving introduction of a vector including the construct into a plant cell. Such introduction should be followed by recombination between the vector and the plant cell genome to introduce the sequence of nucleotides into the genome. RNA encoded by the introduced nucleic acid construct may then be transcribed in the cell and descendants thereof, including cells in plants regenerated from transformed material. A gene stably incorporated into the genome of a plant is passed from generation to generation to descendants of the plant, so such descendants should show the desired phenotype.

The present invention also provides a plant comprising a plant cell as disclosed.

A plant according to the present invention may be one which does not breed true in one or more properties. Plant varieties may be excluded, particularly registrable plant varieties according to Plant Breeders' Rights.

In addition to a plant, the present invention provides any clone of such a plant, seed, selfed or hybrid progeny and descendants, and any part of any of these, such as cuttings, seed.

The present invention may be used in plants such as crop plants, including cereals and pulses, maize, wheat, potatoes, tapioca, rice, sorgum, millet, cassava, barley, pea and other root, tuber or seed crops. Important seed crops are oil seed rape, sugar beet, maize, sunflower, soybean and sorghum. Horticultural plants to which the present invention may be applied may include lettuce, endive and vegetable brassicas including cabbage, broccoli and cauliflower, and carnations and geraniums. The present invention may be applied to tobacco, cucurbits, carrot, strawberry, sunflower, tomato, pepper, chrysanthemum, poplar, eucalyptus and pine.

In relation to use in mammals or other higher animals, DNA vectors (including naked DNA suitable for expression in mammals) of the present invention encode either:

(i) a SARM as described above, or (ii) an anti-sense RNA molecule selected to target a region identified by the SRM-based methods discussed above.

Such vector may be based on any appropriate vector known to those skilled in the art. For instance incorporation of this DNA into mammalian cells to produce such antisense RNA in vivo might be accomplished using vectors based on the disclosure of European patent application 909052736.3 (VICAL), HSV, vaccinia or adenovirus (see Principles of Gene Manipulation (1994) 5th Edit. Old and Primrose 5th Edition, Blackwell Scientific Publications). Viral vectors for use in gene therapy are discussed by Vile (1997) Nature Biotechnology 15: 840-841. A non-viral gene therapy approach is discussed by Sebestyen et al (1998) Nature Biotechnology 16: 80-85. The use of a variety of gene therapy delivery systems (including HSV VP22) is discussed by Fernandez & Baylay (1998) Nature Biotechnology 16: 418-420 and references therein.

Also provided by the present invention is an organism, preferably a non-human mammal, comprising cells in which a target gene is subject to PTGS by use of the SARM-based methods or materials disclosed herein. Particularly preferred is a rodent e.g. murine organism. In this embodiment the invention provides an alternative to known methods of producing 'knock out' mammals in which specific gene activities have been impaired (see e.g. Boerrigter et al (1995) Nature 377: 657-659, or Gossen and Vijk (1993) Trends Genet 9: 27-31.)

The invention will now be further described with reference to the following non-limiting Examples describing work of the inventors. The results are also discussed, and suggestions made as to the origin of the SRMs of the present invention. However it will be appreciated by those skilled in the art that the materials, methods and processes in the present disclosure may be usefully applied irrespective of the precise underlying mechanisms involved.

All references discussed herein, inasmuch as they may be required to supplement the present disclosure, are incorporated herein by reference.

EXAMPLES

Example 1

Detection of SRMs in Silenced Plants

Analyses were performed to detect low molecular weight antisense RNA in four classes of PTGS in plants using the following general methods.

Total RNA was extracted from leaves of tomato, tobacco and *N. benthamiana* as described previously (E. Mueller, J. E. Gilbert, G. Davenport, G. Brigneti, D. C. Baulcombe, *Plant J.* 7, 1001 (1995)). From these preparations, low molecular weight RNA was enriched by ion exchange chromatography on Qiagen columns following removal of high molecular weight species by precipitation with 5% polyethylene glycol (8000)/0.5M NaCl (for tobacco and *N. benthamiana*) or (for tomato) by filtration through Centricon 100 concentrators (Amicon). Low molecular weight RNA was separated by electrophoresis through 15% polyacrylamide/7M urea/0.5× TBE gels, transferred onto Hybond Nx filters (Amersham) and fixed by UV crosslinking.

Prehybridization was in 45% formamide, 7% SDS, 0.3M NaCl, 0.05M $Na_2HPO_4/NaH_2PO_4$ (pH7), 1×Denhardt's solution, 100 $mg.ml.^{-1}$ sheared, denatured, salmon sperm DNA at between 30° C. and 40° C. Hybridization was in the same solution with single stranded RNA probes transcribed with a-$^{32}$P-labelled UTP. Before addition to the filters in the prehybridization solution, probes were hydrolysed to lengths averaging 50 nucleotides. Hybridization was for 16 hours at 30° C. (ACO probes), 35° C. (GUS probe) or 40° C. (GFP and PVX probes).

Sizes of RNA molecules were estimated by comparison with $^{33}$P phosphorylated DNA oligonucleotides run on the same gels but imaged separately. Additionally, samples from different types of PTGS including those discussed were frequently run on the same gel. Alignment of the filters following hybridization with different specific probes confirmed that the PTGS specific signals were identical in size. The probes used are in each case sequence specific. We have observed no cross-hybridization between 25 nt signals in different PTGS systems using either filter hybridisation or RNAase protection.

We do not have an exact measurement of amount of 25 nt per cell, but given the short exposure times routinely used to detect these molecules and taking into account their size, they are likely to be very abundant in cells exhibiting PTGS.

Co-Suppression

The first class tested was transgene-induced PTGS of an endogenous gene ("co-suppression"). We used five tomato lines (T1.1, T1.2, T5.1, T5.2, T5.3), each transformed with a tomato 1-aminocyclopropane-1-carboxylate oxidase (ACO)

cDNA sequence placed downstream of the cauliflower mosaic virus 35S promoter (35S). Two lines (T5.2, T5.3) exhibited PTGS of the endogenous ACO mRNA when amplified by RT-PCR and detected by hybridization with labelled ACO cDNA.

Low molecular weight nucleic acids purified from the five lines were separated by denaturing polyacrylamide gel electrophoresis, blotted, and hybridized to an ACO sense (antisense-specific) RNA probe. More specifically, the low molecular weight RNA and a 30-mer ACO antisense RNA oligonucleotide were fractionated, blotted and hybridized with either ACO sense RNA or antisense RNA transcribed from full length ACO cDNA. The low hybridisation temperature permitted some non-specific hybridization to tRNA and small rRNA species which constitute most of the RNA mass in these fractions. A discrete, ACO antisense RNA of 25 nucleotides (nt) was present in both PTGS lines but absent from the non-silencing lines. 25 nt ACO RNA of sense polarity and at the same abundance as the 25 nt ACO antisense RNA was also present only in the PTGS lines. The 25 nt ACO antisense signal was completely abolished by pretreatment with either RNAaseONE or NaOH.

Transgene Silencing

PTGS induced by transgenes can also occur when a transgene does not have homology to an endogenous gene (1). Therefore we tested whether this type of PTGS was also associated with small antisense RNA. We analysed three tobacco lines carrying 35S-b-glucuronidase (GUS) transgenes. Two of these lines, T4 (15) and 6b5 (16) exhibited PTGS of GUS. The third line (6b5x271) tested was produced by crossing 6b5 with line 271 (17) in which there is a transgene suppressor of the 35S-promoter in 6b5. There was no PTGS of GUS in 6b5x271 due to the transcriptional suppression of the 35S GUS transgene (18).

Hybridization with a GUS-specific probe revealed that low molecular weight GUS antisense RNA was present in T4 and 6b5 but absent from line 6b5x271. 25 nt GUS antisense RNA was detected by hybridizhybridisation with hydrolysed GUS sense RNA transcribed from the 3' 700 bp of the GUS cDNA. The amount of antisense RNA correlated with the degree of PTGS: line 6b5 has stronger PTGS of GUS than line T4 (18) and also had more GUS antisense RNA. It appears that 25 nt antisense GUS RNA is dependent upon transcription from the 35S promoter.

As for PTGS of ACO in tomato, the GUS antisense RNA was a discrete species of approximately 25 nt.

Systemically Induced Transgene Silencing

In some examples of PTGS, silencing is initiated in a localizsed region of the plant. A signal molecule is produced at the site of initiation and mediates systemic spread of silencing to other tissues of the plant (19, 20). We investigated whether systemic PTGS of a transgene encoding the green fluorescent protein (GFP) is associated with 25 nt GFP antisense RNA. PTGS was initiated in *Nicotiana benthamiana* expressing a GFP transgene by infiltration of a single leaf with *Agrobacterium tumefaciens* containing GFP sequences in a binary plant transformation vector.

More specifically, lower leaves of untransformed *N. benthamiana* and *N. benthamiana* carrying an active 35S-GFP transgene (35S-GFP) were infiltrated with *A. tumefaciens* containing the same 35S-GFP transgene in a binary vector. Two to three weeks following this infiltration, the GFP fluorescence disappeared due to systemic spread of PTGS as described previously (11, 20).

RNA from upper, non-infiltrated leaves of these plants and from equivalent leaves of non-infiltrated plants was hybridized with GFP sense RNA transcribed from a full length GFP cDNA. We detected 25 nt GFP antisense RNA in systemic tissues exhibiting PTGS of GFP. It was not detected in equivalent leaves of plants that had not been infiltrated or in non-transformed plants that had been infiltrated with the *A. tumefaciens* i.e. only the transgenic *N. benthamiana* infiltrated with the *A. tumefaciens* accumulated 25 nt GFP antisense RNA.

RNA-Mediated Defense Against Viral Infection

A natural manifestation of PTGS is the RNA-mediated defense induced in virus infected cells (8). Therefore we investigated whether virus-specific, 25 nt RNA could be detected in a virus-infected plant.

A high titre, synchronised PVX infection on leaves of untransformed *N. benthamiana*. was initiated by infiltration of single leaves with *A. tumefaciens* containing a binary plasmid incorporating a 35S-PVX-GFP sequence. Once transcribed, the PVX RNA replicon is independent of the 35S-PVX-GFP DNA, replicates to high levels and moves systemically through the plant. The *A. tumefaciens* does not spread beyond the infiltrated patch and is not present in systemic leaves (20). The GFP reporter in the virus was used to allow visual monitoring of infection progress. We have obtained similar signals with wild type PVX inoculated as virions in sap taken from an infected plant.

RNA was extracted from inoculated leaves after 2, 4, 6 and 10 days and from systemic leaves after 6 and 10 days. RNA was extracted from mock inoculated leaves after 2 days. 25 nt PVX antisense RNA was detected by hybridization with PVX sense RNA transcribed from a full length PVX cDNA. 25 nt RNA complementary to the positive strand (genomic) of potato virus X (PVX) was detected 4 days after inoculation of *N. benthamiana* and continued to accumulate for at least another 8 days in the inoculated leaf. 25 nt PVX RNA but was not detected in mock inoculated leaves.

Discussion

Thus, 25 nt antisense RNA, complementary to targeted mRNAs, is accumulates in four types of PTGS. We have also detected 25 nt RNA in other examples of PTGS as follows: *N. benthamiana* (spontaneous silencing of a 35S-GFP transgene), tomato (35S-ACO containing an internal direct and inverted repeat), petunia (co-suppression of chalcone synthase transgenes and endogenes) and *Arabidopsis thaliana* (PTGS of 35S-GFP by a 35S-PVX-GFP transgene).

However the 25 nt RNA has never been detected in the absence of PTGS. This correlation and the properties of 25 nt RNA are consistent with a direct role for them in PTGS induced by, for instance, transgenes or viruses (12). 25 nt RNA species also serve as molecular markers for PTGS. Their presence could be used to confirm other examples of e.g. transgene or virus-induced PTGS and may also serve to identify endogenous genes that are targeted by PTGS in non-transgenic plants. The 25 nt antisense RNA species are not degradation products of the target RNA because they have antisense polarity. A more likely source of these RNAs is the transcription of an RNA template. This is consistent with the presence of the 25 nt PVX RNA in PVX infected cells that do not contain a DNA template. In a further experiment, low molecular weight RNA was extracted from plants containing silencing (S) or non-silencing (NS), 35S-ACC-oxidase (ACO, tomato) or 35S-GFP (*N. benthamiana*) transgenes. Each was hybridised with $^{32}$P-labelled RNA probes transcribed in the sense orientation from ACC-oxidase and GFP cDNAs and single stranded RNA then removed by digestion with RNAaseONE (Promega). The remaining protected RNA molecules were denatured, separated by electrophoresis on a 15% polyacrylamide/7M urea.0.5×TBE gel. The gel was dried and imaged by autoradiography. "+" and "−" consist of each probe incubated alone with or without subsequent digestion with RNAaseONE. With the ACO probe, protected fragments are obtained only with RNA from the ACO silencing tomato plants and with the GFP probe only with RNA from the GFP silencing plants illustrating the sequence specificity of the signal. The short RNA species detected in this assay correspond to the 25 nt RNA detected by northern analysis but are more disperse because of RNAase digestion at the ends of breathing RNA duplexes. Some higher molecular weight signals were also obtained, possible as a result of incomplete digestion of single stranded regions.

The dependency of 25 nt GUS antisense RNA accumulation on sense transcription of a GUS transgene also supports the RNA template model. An RNA-dependent RNA polymerase, as required by this model, is required for PTGS in *Neurospora crassa* (23). With the present data, we cannot distinguish whether the antisense RNA is made directly as 25 nt species or as longer molecules that are subsequently processed. The precise role of 25 nt RNA in PTGS remains to be determined conclusively. However, as they are long enough to convey sequence specificity yet small enough to move through plasmodesmata, it is probable that they are components of the systemic signal and specificity determinants of PTGS.

Example 2

Detection of SRMs in Silenced Nematodes

RNA from *Caenorhabditis elegans* was obtained from Department of Embryology, Carnegie Institution of Washington, 115 West University Parkway, Baltimore, Md. 21210, USA). RNA was extracted by standard methods known in the art and was concentrated by ethanol precipitation and redissolved in formamide prior to analysis here.

Nematodes were selected which showed either PTGS (by ingestion of *E. coli* which synthesise double stranded GFP RNA) or non-silencing of a GFP transgene.

Northern analysis of this RNA was performed generally as described above. RNA was fractionated by electrophoresis through a 15% polyacrylamide gel containing 7M urea and 0.5×Tris Borate EDTA buffer and electrophoretically transferred onto a Hybond Nx filter (Amersham) The membrane was placed on three layers of 3MM (Whatman) filter paper saturated with 20×SSC for 20 minutes and then allowed to dry at room temperature. The RNA was covalently linked to the membrane by Ultraviolet radiation crosslinking ("autocrosslink" setting in "Stratalinker" apparatus (Stratagene). The membrane was prehybridized 45% formamide, 7% SDS, 0.3M NaCl, 0.05M $Na_2HPO_4/NaH_2PO_4$ (pH7), 1×Denhardt's solution, 100 mg.ml.$^{-1}$ sheared, denatured, salmon sperm DNA at 40° C. Hybridization was in the same solution with a single stranded RNA probe transcribed in the sense orientation with $\alpha$-$^{32}$P-labelled UTP from the entire coding sequence of GFP. Before addition to the filter in the prehybridization solution, the probe was hydrolysed to lengths averaging approximately 50 nucleotides by incubation in 100 mM $Na_2HCO_3/NaH_2CO_3$ (pH 10.2) at 60° C. for 3 hours. Hybridization was for 16 hours 40° C. The membrane was washed at 50° C. in 2×SSC/0.2% SDS and the radioactive signal imaged by a phosphorimager.

As in the previous example, 25 nt. anti-sense RNA was detectable in the silenced material.

REFERENCES

1. H. Vaucheret, et al., *Plant J.* 16, 651-659 (1998).
2. C. Cogoni and, G. Macino, *Trends Plant Sci.* 2, 438-443 (1997).
3. A. Fire, et al., *Nature* 391, 806-811 (1998).
4. J. R. Kennerdell and, R. W. Carthew, *Cell* 95, 1017-1026 (1998).
5. H. Ngo, C. Tschudi, K. Gull, E. Ullu, *Proc. Natl. Acad. Sci. U.S.A.* 95, 14687-14692 (1998).
6. G. Pruss, X. Ge, X. M. Shi, J. C. Carrington, V. B. Vance, *Plant Cell* 9, 859 (1997); R. Anandalakshmi, et al., *Proc. Nati. Acad. Sci. U.S.A.* 95, 13079 (1998); K. D. Kasschau and J. C. Carrington, *Cell* 95, 461 (1998); G. Brigneti, et al., *EMBO J.* 17, 6739 (1998); C. Beclin, R. Berthome, J.-C. Palauqui, M. Tepfer, H. Vaucheret, *Virology* 252, 313 (1998).
7. J. A. Lindbo, L. Silva-Rosales, W. M. Proebsting, W. G. Dougherty, *Plant Cell* 5, 1749-1759 (1993).
8. F. Ratcliff, B. D. Harrison, D. C. Baulcombe, *Science* 276, 1558 (1997); S. N. Covey, N. S. Al-Kaff, A. Langara, D. S. Turner, *Nature* 385, 781 (1997); F. Ratcliff, S. MacFarlane, D. C. Baulcombe, *Plant Cell* 11, 1207 (1999).
9. R. B. Flavell, *Proc. Natl. Acad. Sci. U.S.A.* 91, 3490 (1994).
10. R. A. Jorgensen, R. G. Atkinson, R. L. S. Forster, W. J. Lucas, *Science* 279, 1486 (1998).
11. O. Voinnet, P. Vain, S. Angell, D. C. Baulcombe, *Cell* 95, 177 (1998).
12. D. Grierson, R. G. Fray, A. J. Hamilton, C. J. S. Smith, C. F. Watson, *Trends In Biotechnol.* 9, 122 (1991); W. G. Dougherty, T. D. Parks, *Curr. Opin. Cell Biol.* 7, 399 (1995); D. C. Baulcombe and, J. J. English, *Curr. Opin. Biotechnol.* 7, 173 (1996).
15. S. L. A. Hobbs, T. D. Warkentin, C. M. O. DeLong, *Plant Molecular Biology* 21, 17 (1993).
16. T. Elmayan and, H. Vaucheret, *Plant J.* 9, 787 (1996).
17. H. Vaucheret, C. R. *Acad. Sci. Paris.* 316, 1471 (1993).
18. J. J. English, G. F. Davenport, T. Elmayan, H. Vaucheret, D. C. Baulcombe, *The Plant J.* 12, 597 (1997).
19. O. Voinnet and, D. C. Baulcombe, *Nature* 389, 553 (1997).
20. J.-C. Palauqui, and S. Balzergue, *Curr. Biol.* 9, 59 (1999).
23. C. Cogoni and, G. Macino, *Nature* 399, 166 (1999).

The invention claimed is:

1. A cell comprising at least one synthetic DNA construct that expresses short antisense RNA molecules (SARMs) and short sense RNA molecules (SSRMs), collectively short RNA molecules (SRMs),
   wherein the SSRMs and SARMs consist of 20-30 nucleotides, and
   wherein said SARMs are complementary to, and can base pair with, a target RNA in the cell, which target RNA is transcribed from a gene that is silenced when said SRMs are present in the cell, and said SSRMs correspond to the target RNA.

2. The cell of claim 1 wherein said DNA construct is contained in a vector introduced into said cell.

3. The cell of claim 2 wherein said DNA construct is stably maintained by said cell.

4. The cell of claim 1 wherein the nucleotide sequences of each SSRM and each SARM consists of 20 nucleotides.

5. The cell of claim 1 wherein the nucleotide sequences of each SSRM and each SARM consists of 21 nucleotides.

6. The cell of claim 1 wherein the nucleotide sequences of each SSRM and each SARM consists of 22 nucleotides.

7. The cell of claim 1 wherein said gene to be silenced is selected from the group consisting of a gene involved in cancer, apoptosis, cell-cycle regulation, a neurological process and signal transduction.

8. The cell of claim 1 wherein said gene to be silenced is selected from the group consisting of an oncogene, a pocket protein, a transcriptional regulator and a MHC superfamily member gene.

9. The cell of claim 1 wherein the nucleotide sequences of each SSRM and each SARM consists of 23 nucleotides.

10. The cell of claim 1 wherein the nucleotide sequences of each SSRM and each SARM consists of 24 nucleotides.

11. The cell of claim 1 wherein the nucleotide sequences of each SSRM and each SARM consists of 25 nucleotides.

12. The cell of claim 1 wherein the nucleotide sequences of each SSRM and each SARM consists of 26 nucleotides.

13. The cell of claim 1 wherein the nucleotide sequences of each SSRM and each SARM consists of 27 nucleotides.

14. The cell of claim 1 wherein the nucleotide sequences of each SSRM and each SARM consists of 28 nucleotides.

15. The cell of claim 1 wherein the nucleotide sequences of each SSRM and each SARM consists of 29 nucleotides.

16. The cell of claim 1 wherein the nucleotide sequences of each SSRM and each SARM consists of 30 nucleotides.

* * * * *